(12) United States Patent
Yamashita et al.

(10) Patent No.: US 11,331,451 B2
(45) Date of Patent: May 17, 2022

(54) MEDICAL TUBE, CATHETER AND METHOD OF MANUFACTURING MEDICAL TUBE

(71) Applicant: TERUMO KABUSHIKI KAISHA, Tokyo (JP)

(72) Inventors: Yasunori Yamashita, Fujinomiya (JP); Noriyuki Kitada, Fujinomiya (JP); Hiroki Nagatsu, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 658 days.

(21) Appl. No.: 16/361,682

(22) Filed: Mar. 22, 2019

(65) Prior Publication Data

US 2019/0275290 A1    Sep. 12, 2019

Related U.S. Application Data

(60) Division of application No. 14/314,560, filed on Jun. 25, 2014, now abandoned, which is a continuation of
(Continued)

(51) Int. Cl.
*A61B 8/12* (2006.01)
*A61M 25/00* (2006.01)
(Continued)

(52) U.S. Cl.
CPC .......... *A61M 25/0023* (2013.01); *A61B 8/12* (2013.01); *A61B 8/445* (2013.01); *A61B 8/4461* (2013.01);
(Continued)

(58) Field of Classification Search
CPC ... A61B 2090/3966; A61B 8/12; A61B 8/445; A61B 8/4461; A61M 2025/0183;
(Continued)

(56) References Cited

U.S. PATENT DOCUMENTS 5,622,665 A    4/1997  Wang
5,648,133 A *  7/1997  Suzuki ................. B65D 1/0276
                                                              215/370
(Continued)

FOREIGN PATENT DOCUMENTS

JP    H05-253304 A    10/1993
JP    2003-061963 A    3/2003
(Continued)

OTHER PUBLICATIONS

The extended European search report dated Aug. 7, 2015, by the European Patent Office in corresponding European Patent Application No. 13741402.5 (10 pages).
(Continued)

*Primary Examiner* — Mark D Remaly
(74) *Attorney, Agent, or Firm* — Buchanan Ingersoll & Rooney PC (57)    ABSTRACT

A medical tube includes a distal portion provided on one end side having a first outer diameter, a first inner diameter, and a first thickness; a proximal portion provided on the other end side having a second outer diameter greater than the first outer diameter, a second inner diameter greater than the first inner diameter, and a second thickness greater than the first thickness; and an intermediate portion provided between the distal portion and the proximal portion and having an outer diameter, an inner diameter, and a thickness which gradually
(Continued)

vary. Thus, a medical tube is provided having improved operability and which reduces the likelihood of bending during an operation.

5 Claims, 9 Drawing Sheets

Related U.S. Application Data application No. PCT/JP2013/051071, filed on Jan. 21, 2013.

(51) Int. Cl.
*B29C 48/25* (2019.01)
*A61B 8/00* (2006.01)
*A61M 25/01* (2006.01)
*A61M 25/09* (2006.01)
*B29C 71/00* (2006.01)
*A61B 90/00* (2016.01)

(52) U.S. Cl.
CPC .... *A61M 25/0009* (2013.01); *A61M 25/0021* (2013.01); *A61M 25/0054* (2013.01); *A61M 25/0108* (2013.01); *A61M 25/09* (2013.01); *B29C 48/267* (2019.02); *B29C 71/0063* (2013.01); *A61B 2090/3966* (2016.02); *A61M 25/0045* (2013.01); *A61M 2025/0183* (2013.01); *F04C 2270/0421* (2013.01)

(58) Field of Classification Search
CPC .......... A61M 25/0009; A61M 25/0021; A61M 25/0023; A61M 25/0045; A61M 25/0054; A61M 25/0108; A61M 25/09; B29C 48/267; B29C 71/0063; F04C 2270/0421
See application file for complete search history.

(56) References Cited

U.S. PATENT DOCUMENTS

| 6,524,299 | B1 | 2/2003 | Tran et al. |
| 2004/0122360 | A1 | 6/2004 | Waldhauser et al. |
| 2005/0008806 | A1 | 1/2005 | Schewe et al. |
| 2005/0142314 | A1 | 6/2005 | Burgmeier et al. |
| 2007/0088257 | A1 | 4/2007 | Fisher et al. |
| 2007/0232893 | A1 | 10/2007 | Tanioka |
| 2012/0095446 | A1 | 4/2012 | Oleksy et al. |

FOREIGN PATENT DOCUMENTS

| WO | 96/26825 | A1 | 9/1996 |
| WO | 97/42020 | A1 | 11/1997 |
| WO | 01/43944 | A1 | 6/2001 |
| WO | 2007/054365 | A1 | 5/2007 |

OTHER PUBLICATIONS

International Search Report (PCT/ISA/210) dated Apr. 9, 2013, by the Japanese Patent Office as the International Searching Authority for International Application No. PCT/JP2013/051071.
Singaporean Office Action ("Invitation to Respond to Written Opinion") dated May 11, 2016 by the Intellectual Property Office of Singapore in counterpart Singaporean Patent Application 11201403868S (13 pages in English).
Office Action (Examination report No. 1 for standard patent application) dated Jul. 28, 2017, by the Australian Patent Office in corresponding Australian Patent Application No. 2013213034. (4 pages).

* cited by examiner

MEDICAL TUBE, CATHETER AND METHOD OF MANUFACTURING MEDICAL TUBE

CROSS-REFERENCE TO RELATED APPLICATIONS

This application is a divisional of U.S. patent application Ser. No. 14/314,560 filed on Jun. 25, 2014, which is a continuation of International Application No. PCT/JP2013/051071 filed on Jan. 21, 2013, and claims priority to Japanese Application No. 2012-011535 filed on Jan. 23, 2012, the entire content of all being incorporated herein by reference.

TECHNICAL FIELD

The disclosure here relates to a medical tube, a catheter and a method of manufacturing a medical tube, and, more particularly relates to a medical tube and a catheter which are inserted into a living body such as a blood vessel or a vascular channel, and a method of manufacturing a medical tube.

BACKGROUND DISCUSSION

Imaging diagnosis which have been performed in the past involve inserting an ultrasound catheter having an imaging function into, for example, a blood vessel of a cardiac coronary artery or into a vascular channel of a bile duct.

The imaging diagnostic apparatus can be an intra vascular ultrasound diagnostic apparatus (Intra Vascular Ultrasound: IVUS). Generally, an intra vascular ultrasound diagnostic apparatus includes a probe, installed with an ultrasonic transducer, that is scanned radially in the inside of a blood vessel. A reflection wave (ultrasound echo) reflected by biological tissue of a lumen (e.g., blood vessel lumen) is received by the same ultrasonic transducer, and thereafter, a process of amplification, detection or the like is applied and a cross-sectional image of a blood vessel is created based on the strength of the produced ultrasound echo.

An optical coherence tomography diagnostic apparatus (Optical Coherence Tomography: OCT) has also been utilized as the imaging diagnostic apparatus. The optical coherent tomography diagnostic apparatus is an apparatus in which a probe, installed with an optical fiber attached to a probe provided with an optical lens and an optical mirror at its distal end, is inserted inside of a blood vessel, light is illuminated in the blood vessel while radially scanning the optical mirror which is arranged on the distal side of the optical fiber and a cross-sectional image of the blood vessel is created based on reflection light from biological tissue.

There has relatively recently been proposed an imaging diagnostic apparatus using an optical frequency domain imaging method (Optical Frequency Domain Imaging: OFDI) which is evaluated as a next-generation OCT.

Japanese Unexamined Patent Publication No. 2003-61963 discloses a catheter which is an intra vascular ultrasound diagnostic apparatus. This catheter gradually decreases in outer diameter toward a distal side such that the properties thereof also change relative to insertion, operability, bending resistance (kink resistance), and the like.

However, if an outer diameter rapidly varies along a catheter in an extending direction, flexural rigidity of the catheter is greatly changed. If the flexural rigidity of the catheter is greatly changed, there is a possibility that operability of the catheter and bending resistance during an operation may be degraded.

The disclosure here is directed to solving the above-described problem and to providing a medical tube that can be improved in operability and prevented from bending during the operation.

SUMMARY

A medical tube according to an exemplary embodiment of the disclosure includes a distal portion that is provided on one end side and has a first outer diameter, a first inner diameter, and a first thickness; a proximal portion that is provided on the other end side and has a second outer diameter greater than the first outer diameter, a second inner diameter greater than the first inner diameter, and a second thickness greater than the first thickness; and an intermediate portion that is provided between the distal portion and the proximal portion and has an outer diameter, an inner diameter, and a thickness which gradually vary.

A medical tube which is configured as described above includes a distal portion that is provided on one end side; a proximal portion that has an outer diameter, an inner diameter, and a thickness greater than those of the distal portion; and an intermediate portion that is provided between the distal portion and the proximal portion and has an outer diameter, an inner diameter, and a thickness which gradually vary. Therefore, it is possible to gradually change the flexural rigidity thereof from a proximal side to a distal side. Accordingly, when applying the medical tube to a catheter and the like, it is possible to exhibit a high tracking property inside a living body by the soft distal portion while exhibiting a high pushing-in property by the proximal portion having high rigidity, thereby improving operability, and it is possible to prevent the medical tube from bending as a result of not being rapidly changed in rigidity along an axial direction.

When the outer diameter, the inner diameter, and the thickness in the intermediate portion gradually vary so as to decrease from the proximal portion side toward the distal portion side, it is possible to gradually lower the flexural rigidity from the proximal side to the distal side in the intermediate portion which varies in size, and it is also possible to achieve improvement in operability and suppression of bending.

When the medical tube is formed of a crystalline resin, it is possible to easily form a shape in which the outer diameter, the inner diameter, and the thickness gradually decrease toward the distal side utilizing a shape changing of the crystalline resin by annealing. In addition, it is possible to promote crystallinity by the annealing, and thus, utilizing characteristics of the crystalline resin wherein the rigidity varies depending on crystallinity, it is possible to change the rigidity of the medical tube depending on a section.

When the distal portion is lower in crystallinity than the proximal portion, it is possible to configure the distal portion having low crystallinity to be soft and likely to be deformed, and configure the proximal portion having high crystallinity unlikely to be deformed, and thus, it is possible to further improve the operability.

When the catheter has a sheath that is configured with the above-described medical tube and configured to be inserted into a lumen, a steering unit configured to be connected to a proximal side of the sheath and to be arranged on a hand side of a user, and an imaging core configured to advance and retreat inside the sheath and to create an image inside the lumen, when inserting the sheath into the lumen, since the sheath is configured with the above-described medical tube, it is possible to exhibit the high tracking property inside the living body by the soft distal portion while exhibiting the high pushing-in property by the proximal portion having the high rigidity, thereby improving operability, and it is possible to prevent the medical tube from bending without being rapidly changed in rigidity along an axial direction. Therefore, the imaging core smoothly performs movements of advancing and retreating.

When a method of manufacturing a medical tube includes a molding step of molding a tubular intermediate body with a crystalline resin in which a thickness of a first section on one side is less than a thickness of a second section on the other side, an outer diameter of the first section is equal to or less than an outer diameter of the second section, and a third section gradually varying in thickness between the first section and the second section is formed; and an annealing step of forming a distal portion which is provided on one end side and has a first outer diameter, a first inner diameter, and a first thickness, a proximal portion which is provided on the other end side and has a second outer diameter greater than the first outer diameter, a second inner diameter greater than the first inner diameter, and a second thickness greater than the first thickness, and an intermediate portion which is provided between the distal portion and the proximal portion and of which an outer diameter, an inner diameter, and a thickness gradually vary, by annealing the intermediate body to promote crystallization, it is possible to easily manufacture the medical tube having the above-described shape by utilizing characteristics of the crystalline resin wherein a diameter is likely reduced as a thickness of a section becomes thin when the annealing is performed, and by annealing the intermediate body including the first section having a thickness less than that of the second section.

When an inner diameter of the intermediate body is constant from the first section to the second section, it is possible to easily form the intermediate body. Then, by simply performing the annealing of the intermediate body wherein the inner diameter is constant, and by utilizing the characteristics of the crystalline resin in which a diameter is likely reduced as a thickness of a section becomes thin when the annealing is performed, it is possible to easily manufacture a member which differs in an outer diameter, an inner diameter, and a thickness depending on a section.

When the intermediate body is molded by extrusion molding in the molding step, it is possible to easily manufacture an intermediate body which differs in a diameter depending on a section.

When time for annealing the first section is shorter than time for annealing the second section in the annealing step, it is possible to enhance crystallinity to be greater on the proximal side than on the distal side of the medical tube to be manufactured, and to enhance the flexural rigidity to be greater on the proximal side than on the distal side.

DETAILED DESCRIPTION

Set forth below is a description of exemplary embodiments of the catheter disclosed here. For purposes of convenience and ease in illustration, the size ratio of various parts and features of the catheter illustrated in the drawing figures is exaggerated and is not intended to be an accurate representation of the actual relative sizes.

Figure 1:
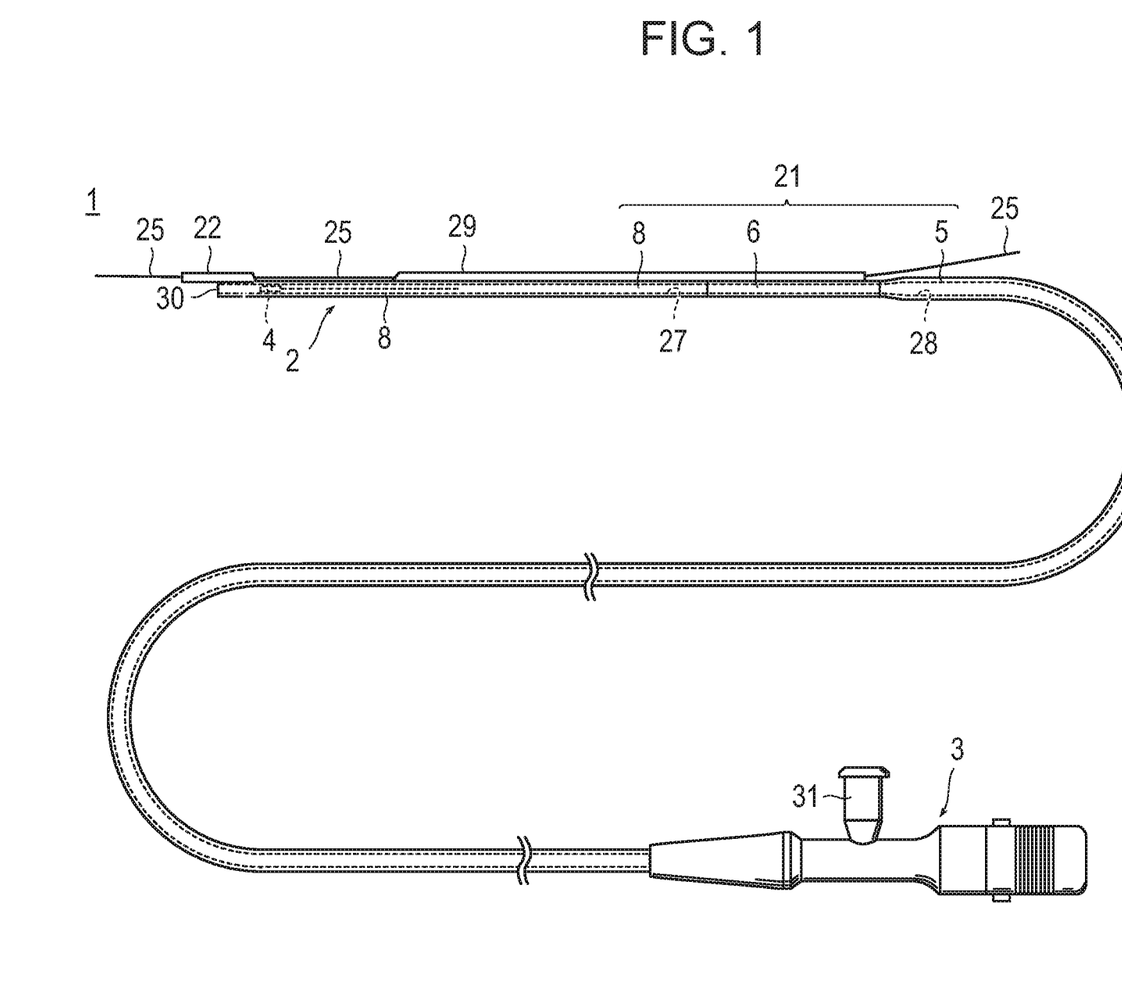
FIG. 1 is a plan view illustrating an ultrasound catheter to which is applied a proximal tube (medical tube) according to an exemplary embodiment of the disclosure.

A medical tube according to an exemplary embodiment of the disclosure herein is a proximal tube 5 applied to an ultrasound catheter 1 which transceives ultrasound waves inside a blood vessel using a built-in ultrasonic transducer and creates a cross-sectional image of the blood vessel. The ultrasound catheter 1, as shown in FIG. 1, includes a sheath 2 sized for insertion into a body cavity, an imaging core 4 for transmitting and receiving ultrasound with respect to a tissue in the body cavity, and a hub 3 through which the imaging core 4 passes. The hub 3 is positioned on the proximal side from the sheath 2.

Figure 2:
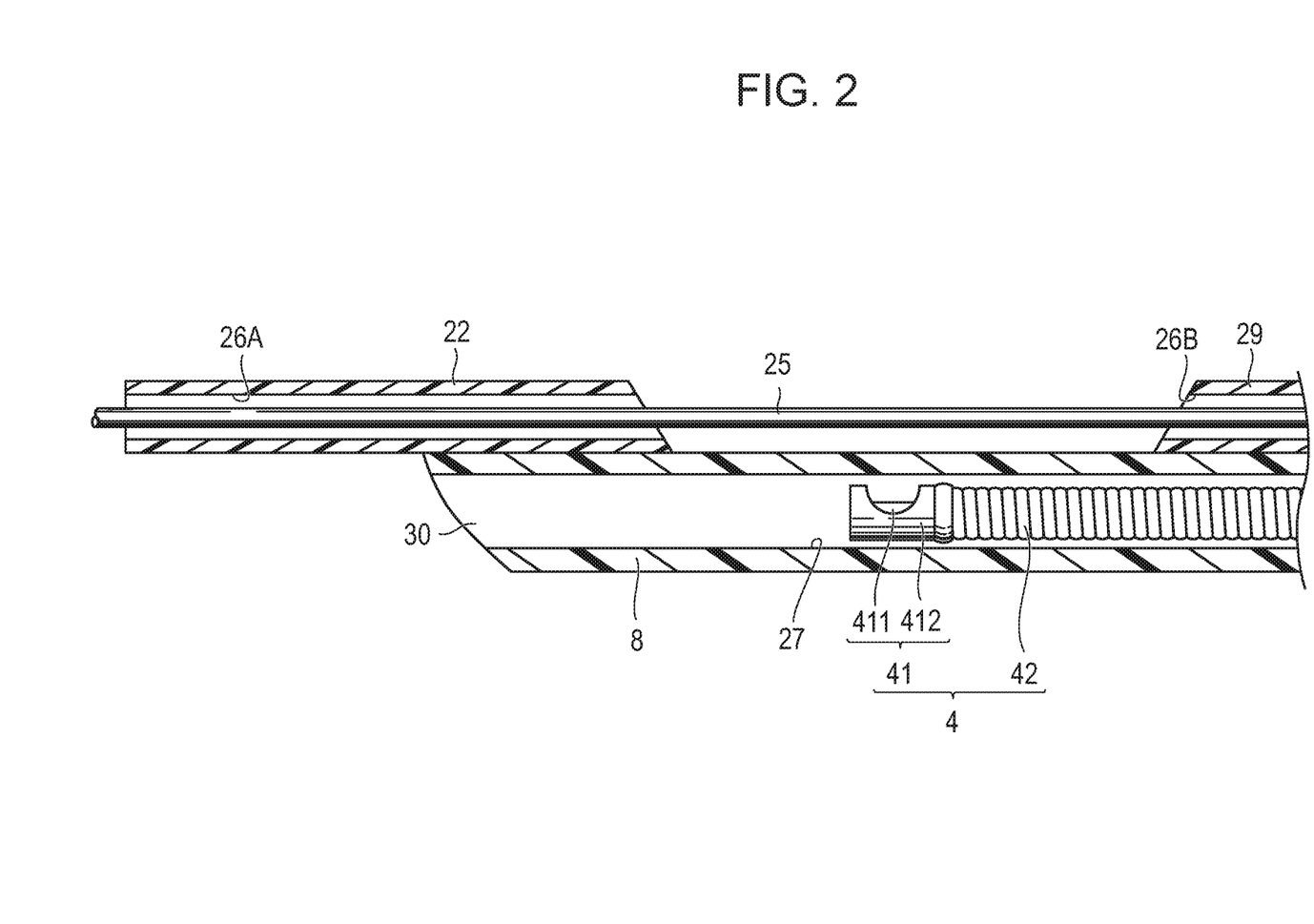
FIG. 2 is a cross-sectional view in the longitudinal direction illustrating a distal portion of the ultrasound catheter.
Figure 3:
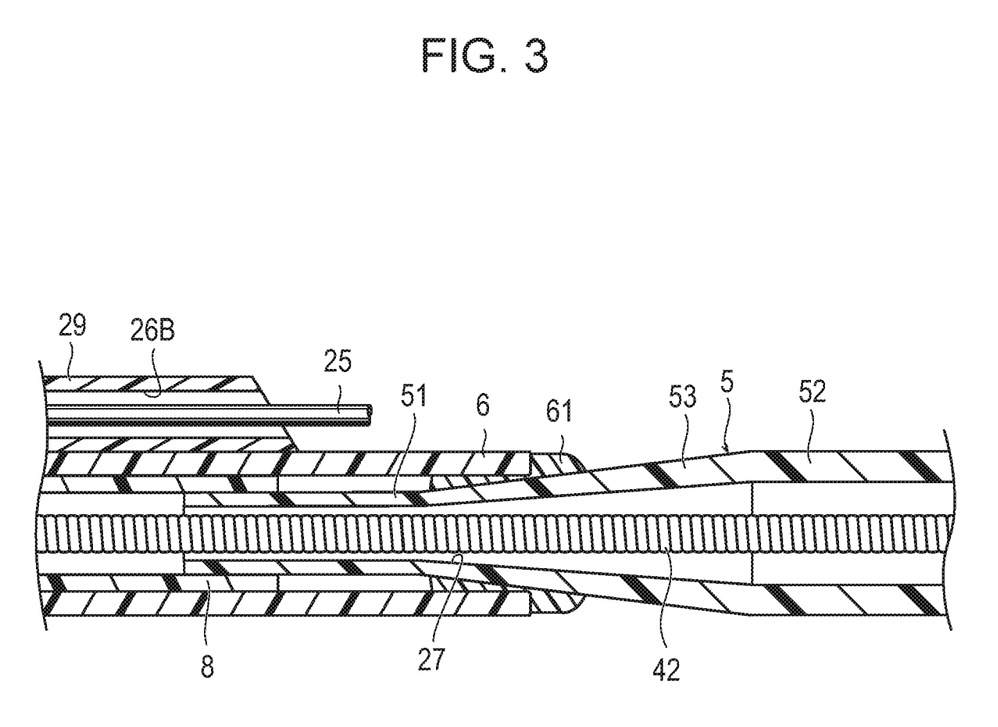
FIG. 3 is a cross-sectional view in the longitudinal direction illustrating the vicinity of a distal portion of the proximal tube of the ultrasound catheter.

The sheath 2, as shown in FIGS. 1 to 3, includes a sheath main body portion 21 connected to a hub 3, a distal tube 22 which is connected to a distal side of the sheath main body portion 21 and in which a first guide wire lumen 26A is formed, and an intermediate tube 29 which is connected to the sheath main body portion 21 to be closer to a proximal side than the distal tube 22 and in which a second guide wire lumen 26B is formed. The sheath main body portion 21 includes the proximal tube 5 (medical tube) connected to the hub 3, a distal outer tube 6 which is interlocked with a distal side of the proximal tube 5 and bonded to an outer side surface of the proximal tube 5, and a distal inner tube 8 which is arranged inside the distal outer tube 6 and communicates with a lumen of the proximal tube 5. The distal tube 22 is fused on an outer side surface of the distal inner tube 8, and the intermediate tube 29 is fused on an outer side surface of the distal outer tube 6.

A guide wire 25 is inserted into the vicinity of an affected area inside a living body in advance, i.e., before inserting the ultrasound catheter 1 inside the living body, and is thus used to guide the ultrasound catheter 1 to the affected area. The ultrasound catheter 1 is guided to the affected area as the guide wire 25 passes through the guide wire lumens 26A and 26B of the ultrasound catheter 1.

Observation portion lumens 27 and 28 which communicate with each other are provided in the distal inner tube 8 and the proximal tube 5. The imaging core 4 is arranged inside the observation portion lumens 27 and 28. The imaging core 4 includes a transducer unit 41 for transceiving the ultrasound waves with respect to tissue inside the lumen, and a drive shaft 42 to which the transducer unit 41 is attached at the distal end and which transmits rotary power thereto.

The transducer unit 41, as illustrated in FIG. 2, has an ultrasonic transducer 411 that transceives the ultrasound waves, and an ultrasonic transducer housing 412 that contains the ultrasonic transducer 411.

The ultrasonic transducer 411 irradiates the ultrasound waves toward the inside of the human body and enables an ultrasonogram of the affected area to be formed by receiving the returning ultrasound waves after they are reflected. In the exemplary embodiment shown, the ultrasonic transducer housing 412 is formed in a concave shape and holds the ultrasonic transducer 411 in a concave portion of the concave shape to protect the ultrasonic transducer 411.

The drive shaft 42 is soft and functions such that rotary power generated in the hub 3 can be transmitted to the transducer unit 41. The drive shaft 42 is configured to be constant in outer diameter with a multi-layer coil-shaped tube such as a three-layer coil in which three coils are layered to be alternately reversed in a winding direction. The drive shaft 42 transmits the rotary power to rotate the transducer unit 41 around an axis extending in a direction of the observation portion lumen 27. Thus, it is possible to observe at 360 degrees the affected area inside the lumen such as a blood vessel and a vascular channel. In addition, the drive shaft 42 has a signal wire passing through the inside thereof to transmit a signal detected by the transducer unit 41 to the hub 3.

In addition, the observation portion lumens 27 and 28 have the imaging core 4 disposed in a built-in manner and they also serve as a path for an ultrasound transmission liquid which is injected from a port 31 of the hub 3. The ultrasound transmission liquid supplied from the port 31 passes through the inside of the observation portion lumens 27 and 28 to fill the sheath 2 from a proximal side to a distal side as it flows therethrough. When injecting the ultrasound transmission liquid, internal air is discharged from a discharge port 30 provided in the distal inner tube 8.

The ultrasound transmission liquid is distributed between the ultrasonic transducer 411 and an inner surface of the sheath 2 by inserting the transducer 411 into the sheath 2 and the like after filling the ultrasound transmission liquid into the sheath 2. Thus, it is possible to cause the ultrasound waves to be transmitted to the affected area (vascular wall) through the ultrasound transmission liquid and blood and to return from the affected area after being reflected. Due to the presence of the ultrasound transmission liquid, the transducer unit 41 can acquire an image signal through the ultrasound waves. Since the ultrasonic transmission liquid can flow into and communicate with an interior of the blood vessel through the discharge port 30 provided in a sheath distal portion 24, a physiological salt solution and the like having no effect on the human body are preferably employed as the ultrasound transmission liquid.

Of further note, an X-ray contrast marker may be provided in the distal tube 22, the distal outer tube 6 or the distal inner tube 8 so as to be able to check a distal position of the ultrasound catheter during X-ray illumination when being inserted into a living body.

Although the first guide wire lumen 26A and the second guide wire lumen 26B are not connected to each other, guide wire paths formed by each of the lumens are arranged to be substantially linear. Therefore, the guide wire 25 can linearly pass through the guide wire lumens 26A and 26B without being bent.

The first guide wire lumen 26A is provided closer to the distal side than the transducer unit 41 of the imaging core 4, and the second guide wire lumen 26B is provided on the proximal side. Therefore, no guide wire lumen is present on an outer peripheral surface of the sheath distal portion 24 which is a channel of the ultrasound waves, and thus, transceiving of the ultrasound waves by the transducer unit 41 is not disturbed by the guide wire lumens 26A and 26B.

With reference to FIG. 3, a specific structure of the sheath main body portion 21 will be described below.

The proximal tube 5 includes a distal portion 51 formed on the distal side, a proximal portion 52 formed on the proximal side, and an intermediate portion 53 formed between the distal portion 51 and the proximal portion 52. In addition, the proximal tube 5 is a tubular body extending from the hub 3 to the vicinity of the proximal side of the second guide wire lumen 26B, and preferably made from a polyether ether ketone (PEEK). The polyether ether ketone is a crystalline thermal plastic resin which is excellent in mechanical strength, chemical resistance, and heat resistance.

The proximal tube 5 is not limited to being formed from polyether ether ketone, and for example, it is possible to use a polyolefin-based resin such as a polyethylene, a polypropylene, a polybutene, a vinyl chloride, an ethylene-vinyl acetate copolymer or a polyolefin-based elastomer of these; a fluorine-based resin or a fluorine-based elastomer; a methacrylic resin; a polyphenylene oxide; a modified polyphenylene ether; a polyethylene terephthalate; a polybutylene terephthalate; a polyamide-imide; a polyether imide; a polyether sulfone; a cyclic polyolefin; a polyurethane-based elastomer; a polyester elastomer; a polyamide or a polyamide-based elastomer; a polycarbonate; a polyacetal; a styrene-based resin or a styrene-based elastomer; a thermoplastic polyimide; and the like.

The distal outer tube 6 is a tubular body interlocked with the distal portion 51 of the proximal tube 5 and extends to the middle of the section where the intermediate tube 29 is provided so as to define an outermost layer. An inner surface of a proximal side of the intermediate tube 29 is fused or bonded to an outer surface of the distal outer tube 6 (refer to FIGS. 1 and 3). The distal outer tube 6 is made from a polyethylene having rigidity lower than that of the material of the proximal tube 5. The distal outer tube 6 and the proximal tube 5 are bonded to each other by an adhesive 61 applied from the proximal side of the distal outer tube 6 to the proximal side of the distal inner tube 8. The adhesive 61 is an ultraviolet curing-type resin, but is not particularly limited hereto as long as it is capable of bonding.

The distal inner tube 8 arranged inside of the distal outer tube 6 is a tubular body which extends from the distal portion 51 of the proximal tube 5 to the distalmost end where the discharge port 30 is formed (refer to FIGS. 1 and 2). The distal inner tube 8 is made from a polyethylene having a rigidity lower than that of the material of the proximal tube 5. In the distal inner tube 8, the distal portion 51 of the proximal tube 5 is pressed therein on the proximal side, an end portion on the distal side defines a distal end of the sheath main body portion 21, and the distal tube 22 is fused on the outer peripheral surface thereof. The distal inner tube 8 may also be bonded to the distal tube 22 using an adhesive without fusing.

The distal inner tube 8 pressed into the distal outer tube 6 from the proximal side to the middle of the section where the intermediate tube 29 is provided. However, since the distal outer tube 6 is not present on the distal side thereof, the distal inner tube 8 defines the outermost layer, thereby causing the outer surface of the distal inner tube 8 to be fused to the intermediate tube 29 (refer to FIGS. 1 and 2). The distal inner tube 8 is also fused to an inner peripheral surface of the distal outer tube 6 or the distal inner tube 8 may be bonded using an adhesive without fusing.

The positional relationships of the proximal tube 5, the distal outer tube 6, the distal inner tube 8, and the intermediate tube 29 are best described as follows. An end portion on the proximal side of the intermediate tube 29 is positioned in the vicinity on the proximal side of the distal outer tube 6. In addition, the intermediate portion 53 of the proximal tube 5 is positioned on the proximal side of the distal outer tube 6. An end portion on the proximal side of the distal inner tube 8 is positioned on the proximal side of the intermediate tube 29 and on an outer periphery of the distal portion 51 of the proximal tube 5.

The material of the distal outer tube 6, the distal inner tube 8, the distal tube 22, and the intermediate tube 29 is not limited to a polyethylene as long as it is a material having a rigidity lower than that of the proximal tube 5, and for example, it is possible to apply a polypropylene, a polyisoprene, a chlorinated polyethylene, a polyvinyl chloride, a polybutadiene, a polystyrene, an anti-shock polystyrene, an acrylonitrile-styrene resin (AS resin), an acrylonitrile-butadiene-styrene resin (ABS resin), a methyl methacrylate-butadiene-styrene resin (MBS resin), a methyl methacrylate-acrylonitrile-butadiene-styrene resin (MABS resin), an acrylonitrile-acrylic rubber-styrene resin (AAS resin), an acrylic resin, a polyester (a polyethylene terephthalate, a polybutylene terephthalate, a polyethylene naphthalate, and the like), a polycarbonate, a polyphenylene ether, a modified polyphenylene ether, an aliphatic polyamide, an aromatic polyamide, a polyphenylene sulfide, a polyimide, a polyether ether ketone, a polysulfone, a polyarylate, a polyether ketone, a polyether nitrile, a polythioether sulfone, a polyether sulfone, a polybenzimidazole, a polyamide-imide, a polyether imide, a polyacetal, a liquid crystal polymer, a thermo-plastic polyurethane, and the like. In addition, the distal outer tube 6 and the proximal tube 5 are fixed to each other by the adhesive 61. However, the distal outer tube 6 and the proximal tube 5 may be fused to each other if fusing is possible depending on the material.

The proximal tube 5 according to the exemplary embodiment, as described above and illustrated in FIG. 4, includes the distal portion 51 formed on the distal side, the proximal portion 52 formed on the proximal side, and the intermediate portion 53 formed between the distal portion 51 and the proximal portion 52.

Figure 4:
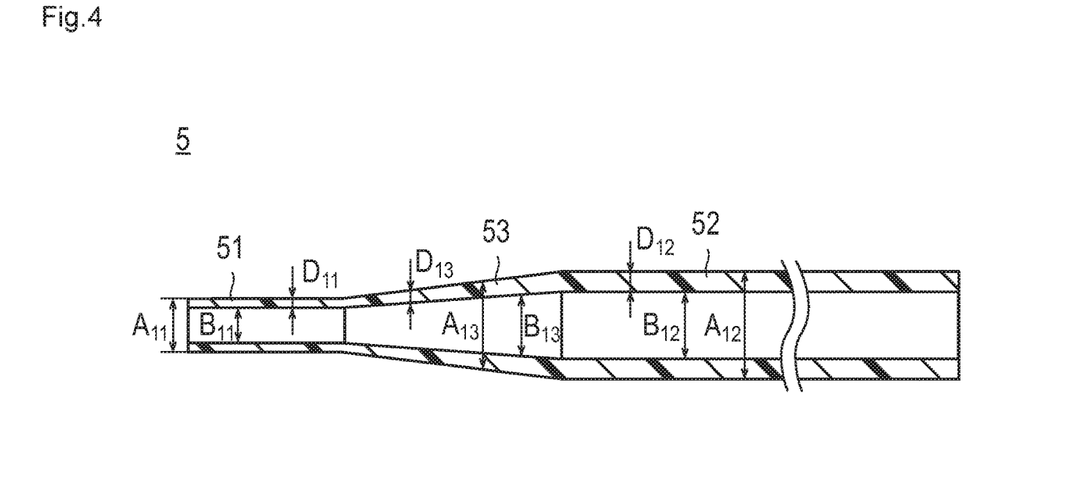
FIG. 4 is a cross-sectional view in the longitudinal direction illustrating the proximal tube according to an exemplary embodiment of the disclosure.

The distal portion 51 has a first outer diameter A11, first inner diameter B11, and a first thickness D11. The proximal portion 52 has a second outer diameter A12 greater than the first outer diameter A11, a second inner diameter B12 greater than the first inner diameter B11, and a second thickness D12 greater than the first thickness D11.

The intermediate portion 53 is provided between the distal portion 51 and the proximal portion 52, and an outer diameter, an inner diameter, and a thickness of the intermediate portion 53 vary to gradually decrease from the proximal side toward the distal side. Therefore, the intermediate portion 53 has a third outer diameter A13 greater than the first outer diameter A11 and less than the second outer diameter A12, a third inner diameter B13 greater than the first inner diameter B11 and less than the second inner diameter B12, and a third thickness D13 greater than the first thickness D11 and less than the second thickness D12.

A crystallinity of the resin forming distal portion 51 is lower than that of the proximal portion 52. Crystallinity of the intermediate portion 53 is higher than crystallinity of the distal portion 51 and lower than crystallinity of the proximal portion 52. It is preferable that crystallinity become lower from the proximal side toward the distal side. Since a crystalline resin becomes lower in rigidity as crystallinity is lowered, the proximal side is unlikely deformed and the crystalline resin is more likely deformed the closer it is to the distal side. Crystallinity can be measured by a known density method, an X-ray diffraction method, an infrared method, an NMR method, a thermal analysis method, and the like.

A method of manufacturing the proximal tube 5 according to an exemplary embodiment of the disclosure is described below.

Figure 5:
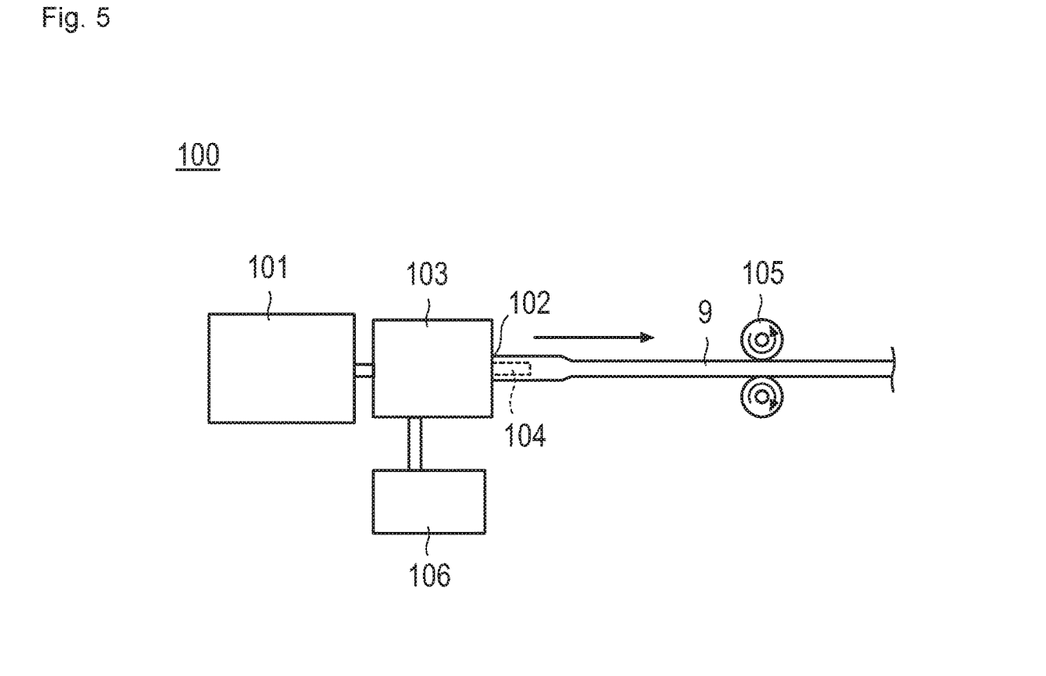
FIG. 5 is a schematic view illustrating an extrusion molding apparatus.

First, a material of the proximal tube 5 is heated and melted, thereby molding a cylindrical intermediate body 9 of which an outer diameter varies stepwise by a known extrusion molding method (molding step). To describe the extrusion molding method briefly, the intermediate body 9 is molded using an ordinary extrusion molding apparatus 100 illustrated in FIG. 5. The extrusion molding apparatus 100 includes an extruder 101 which extrudes a material being heated and melted, a die 103 which extrudes a resin extruded from the extruder 101 from an annular extrusion port 102, a hollow mandrel 104 which is positioned in the center of the extrusion port 102, a hauler 105 which hauls a molded object extruded from the die 103, and a compressor 106 which supplies air into the mandrel 104. The material heated and melted by the extruder 101 is supplied to the die 103 to be continuously extruded from the extrusion port 102 in a tubular shape. Then, the extruded material is subject to sizing to have a constant inner diameter using the mandrel 104 and as a hauling speed of the hauler 105 is changed it is possible to arbitrarily change an outer diameter of the extruded molding object.

Figure 6:
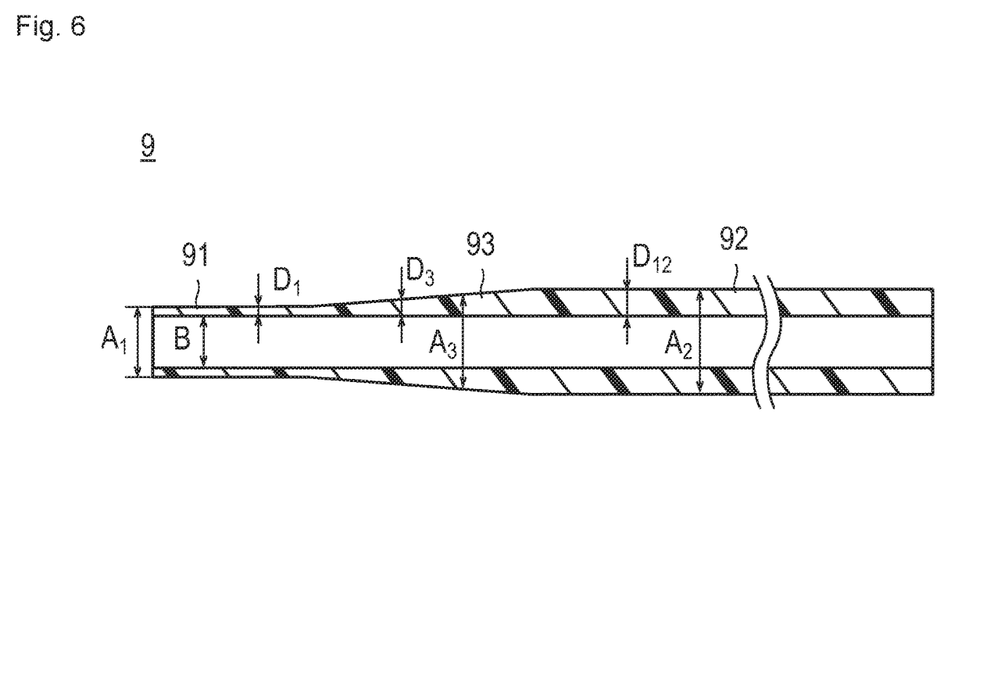
FIG. 6 is a cross-sectional view in the longitudinal direction illustrating an intermediate body which is molded by extrusion molding.

In the intermediate body 9, as illustrated in FIG. 6, a small diameter portion 91 (first section) of an outer diameter A1 is formed on one end side, a large diameter portion 92 (second section) of an outer diameter A2 which is greater than the diameter of the small diameter portion 91 is formed on the other side, and an inclined portion 93 (third section) of which an outer diameter is gradually decreased from the large diameter portion 92 toward the small diameter portion 91 is formed between the small diameter portion 91 and the large diameter portion 92. Note that, the inner diameters B of the large diameter portion 92, the small diameter portion 91, and the inclined portion 93 are constant. Alternatively, in order to mold a tubular intermediate body 9 wherein the outer diameter varies stepwise, a portion on the outer periphery thereof may be scraped after extrusion molding of the tubular body having the constant inner diameter and outer diameter.

Next, the intermediate body 9 is subjected to annealing (heat treatment) to promote crystallization of the material of the intermediate body 9 which is an extrusion molding object having low crystallinity (annealing step). An annealing temperature is within a range approximately from 150 degrees to 300 degrees in a case of a polyether ether ketone.

Annealing time is within a range approximately from 0.1 hours to 5 hours in the case of the polyether ether ketone. As appreciated by one skilled in the art, the temperature and time of annealing are appropriately changed in accordance with a material, a shape, a size, and the like.

When the annealing step is performed, the intermediate body 9 is contracted and deformed, thereby ultimately forming the proximal tube 5. In deformation by annealing, the thickness itself does not significantly change, and the diameter is more likely contracted as the thickness of a section becomes thinner. Therefore, a value for a size in each section is acquired by dividing a size before the annealing by a size after the annealing becomes large on the distal side in which the thickness is thinner than the proximal side and degree of contraction is large, thereby realizing relationships as follows.

$$A1/A11 > A2/A12 \quad \text{Expression (1)}$$

$$B/B11 > B/B12 \quad \text{Expression (2)}$$

$$D1/D11 \approx D2/D12 \quad \text{Expression (3)}$$

Therefore, even if the intermediate body 9 before annealing is molded to have the constant inner diameter B, the distal side having a small thickness becomes less in the inner diameter than that of the proximal side after the annealing, and thus, the inner diameter B11 of the distal portion 51 of the proximal tube 5 becomes less than the inner diameter B12 of the proximal portion 52. Then, in the intermediate body 9, the inclined portion 93 which gradually varies in the outer diameter A3 and the thickness D3 becomes the intermediate portion 53 which is gradually decreased toward the distal side in all of the outer diameter A13, the inner diameter B13, and the thickness D13 after the annealing. In this manner, by only performing the annealing of the intermediate body 9 of which the outer diameter is different depending on a section and the inner diameter is constant, it is possible to easily manufacture the proximal tube 5 which varies in the outer diameter, the inner diameter, and the thickness. Thus, it is possible to easily manufacture such an intermediate body 9 by the extrusion molding.

Figure 7:
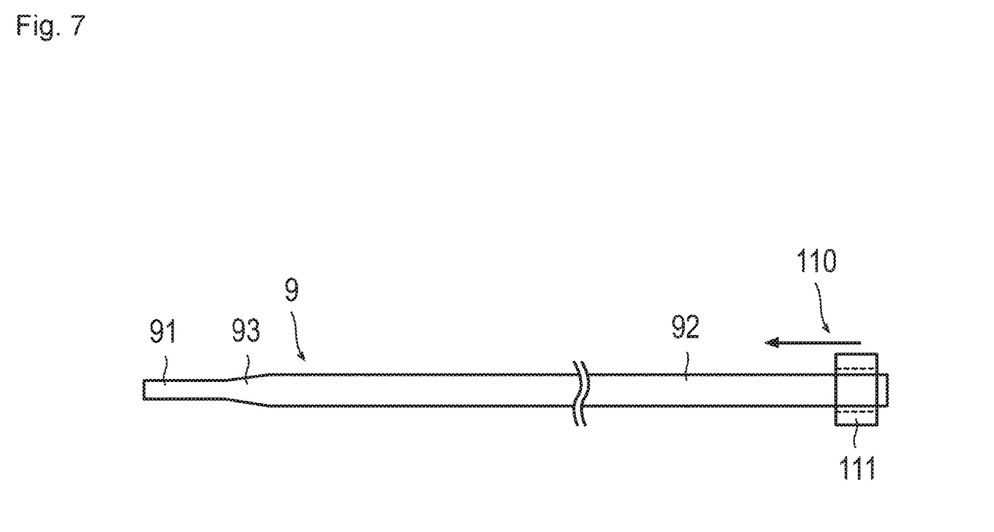
FIG. 7 is a plan view illustrating a state when annealing the intermediate body.

It is preferable that the annealing be performed to be as long as the proximal portion 52 and as short as the distal portion 51 using a heating apparatus 110 illustrated in FIG. 7. The heating apparatus 110 includes an annular heater 111 which heats the intermediate body 9 from an outer side, and the heater 111 is relatively movable with respect to the intermediate body 9 along the intermediate body 9 in the axial direction. The heater 111 is gradually moved from the proximal side to the distal side to perform the annealing for each section. As the heater 111 moves to the distal side, the moving speed is raised. Then, the proximal side of the intermediate body 9 on which the annealing time is long becomes higher in crystallinity than the distal side on which the annealing time is short, and thus, the rigidity on the proximal side becomes high and the rigidity on the distal side becomes low. Although a case of moving the heater 111 from the proximal side to the distal side is described here, naturally, it is also possible to move the heater 111 from the distal side to the proximal side and perform the annealing.

Hence, the outer diameter, the inner diameter, and the thickness are changed along the inclination, and crystallinity is changed as well along the inclination. Thus, it is possible to apply various physical properties (flexural rigidity and the like), thereby amplifying flexibility in the design.

Figure 8:
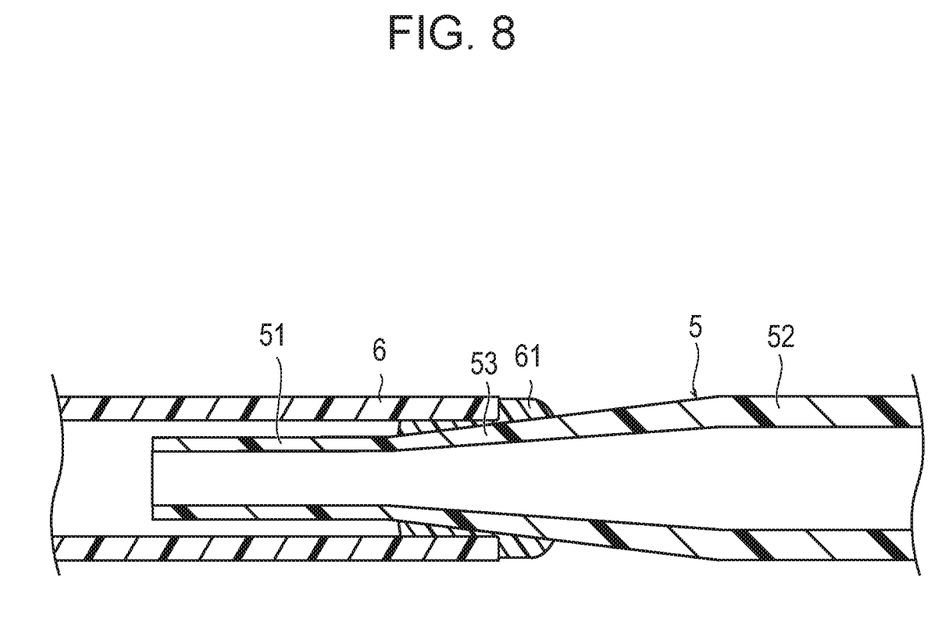
FIG. 8 is a cross-sectional view in the longitudinal direction illustrating a step of bonding the proximal tube and a distal outer tube.
Figure 9A:
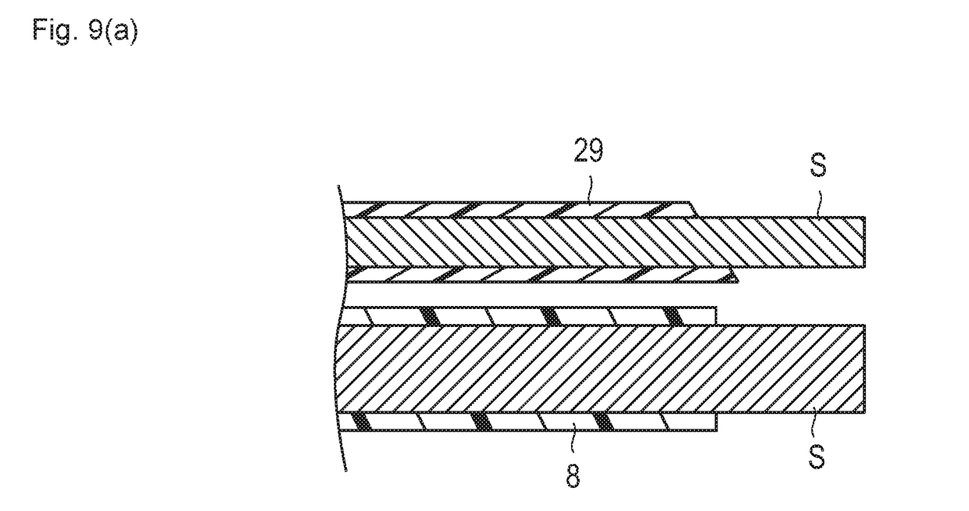
FIGS. 9A and 9B are cross-sectional views in the longitudinal direction illustrating a step of heat-fusing a distal inner tube and an intermediate tube, respectively.
Figure 9B:
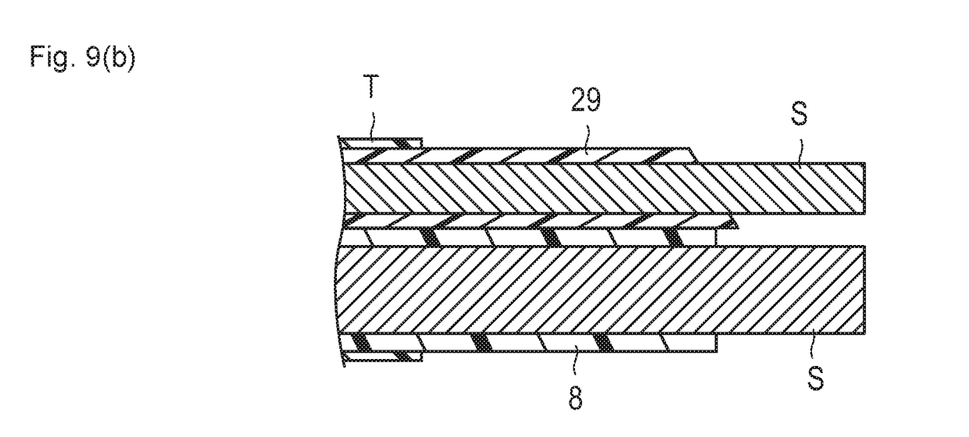
Figure 10A:
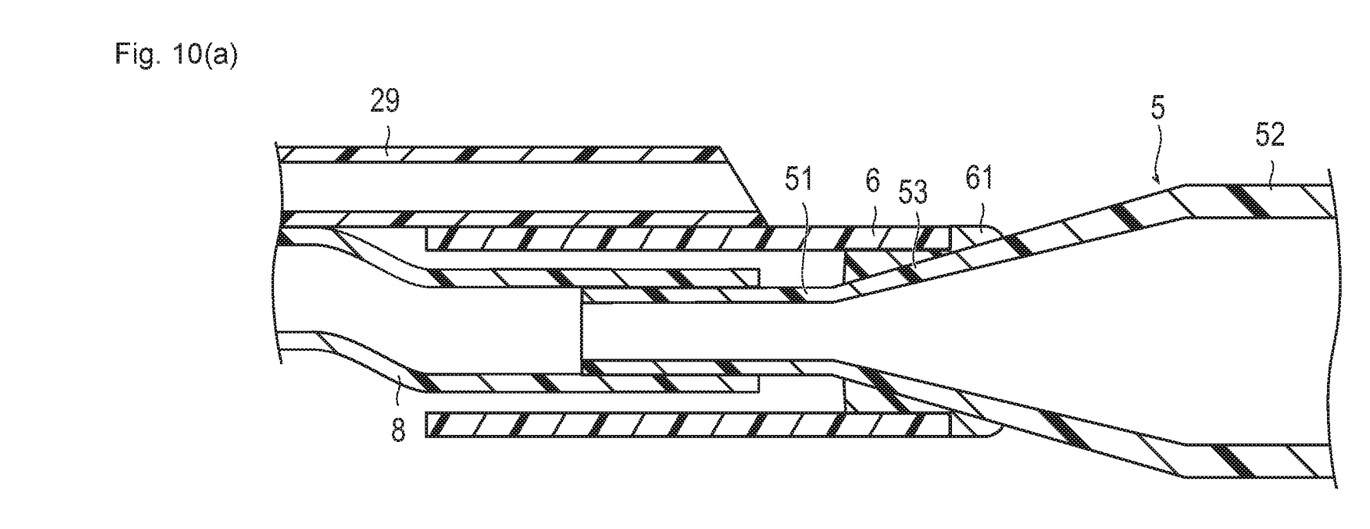
FIGS. 10A and 10B are cross-sectional views in the longitudinal direction illustrating a step of heat-fusing an assembly in which the proximal tube and the distal outer tube are bonded and an assembly in which the distal inner tube and the intermediate tube are heat-fused, respectively.
Figure 10B:
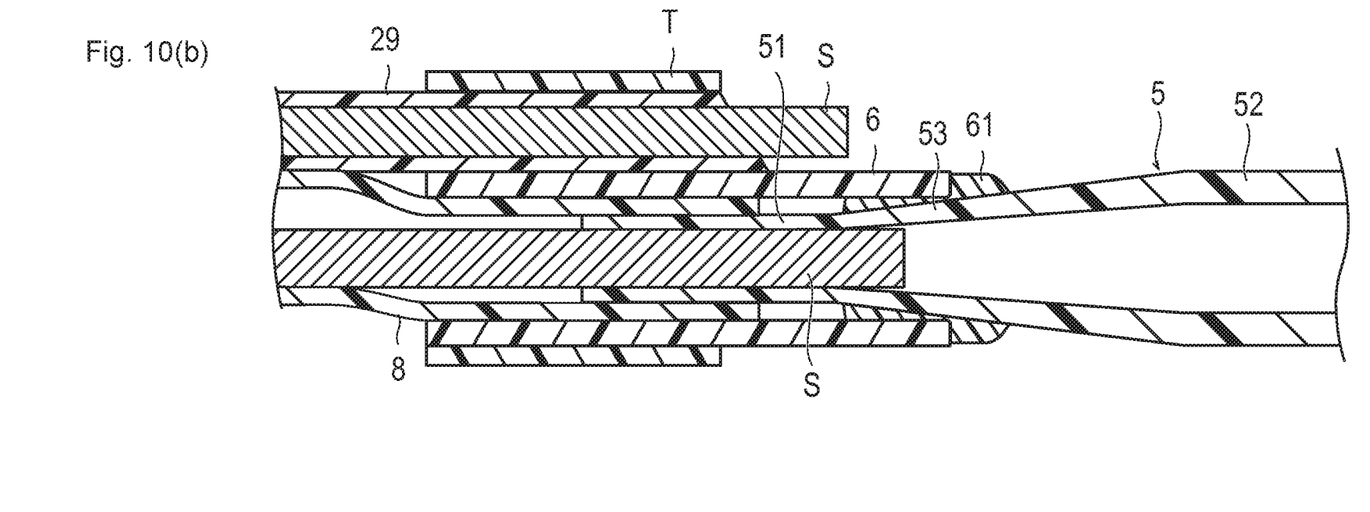

With reference to FIGS. 8 to 10, a method of manufacturing the ultrasound catheter 1 by connecting an assembly of the proximal tube 5 and the distal outer tube 6 and an assembly of the distal inner tube 8 and the intermediate tube 29 according to the exemplary embodiment of the disclosure will be described.

First, as illustrated in FIG. 8, an end portion of the distal outer tube 6 on the proximal side and the intermediate portion 53 of the proximal tube 5 are bonded using the adhesive 61. Next, as illustrated in FIG. 9(a), a core metal S is inserted into the intermediate tube 29 and the distal inner tube 8, and thereafter, as illustrated in FIG. 9(b), the intermediate tube 29 and the distal inner tube 8 are moved closer to each other, thereby performing the heat fusion by covering the outer periphery of the intermediate tube 29 and the distal inner tube 8 with a contraction tube T. A method of the heat fusion is ultrasonic heating, for example. The method of the heat fusion is not limited thereto, however, and it may be performed by induction heating employing a coil. After the heat fusion, the contraction tube T is cut off and can be discarded. Note, however, that the contraction tube T may remain in a state of covering the intermediate tube 29 and the distal inner tube 8 without being discarded. Next, as illustrated in FIG. 10(a), the distal portion 51 of the proximal tube 5 is inserted into the distal inner tube 8, and the distal portion of the distal outer tube 6 is inserted between the intermediate tube 29 and the distal inner tube 8 from the proximal side of the distal inner tube 8 to be abutted against a position where the heat fusion is performed in FIG. 9(b). Then, as illustrated in FIG. 10(b), the core metal S is inserted into the intermediate tube 29, the distal inner tube 8, and the distal portion 51 of the proximal tube 5, and the contraction tube T covers the outer periphery of the intermediate tube 29 and the distal outer tube 6 to perform the heat fusion. After the heat fusion, the contraction tube T is cut off and can be discarded. Note, however, that the contraction tube T may remain in the state of covering the intermediate tube 29 and the distal outer tube 6 without being discarded.

According to the proximal tube 5 in the exemplary embodiment, the proximal tube 5 has the distal portion 51 which is provided on one side; the proximal portion 52 of which the outer diameter, the inner diameter, and the thickness are greater than those of the distal portion 51; and the intermediate portion 53 which is provided between the distal portion 51 and the proximal portion 52 and of which the outer diameter, the inner diameter, and the thickness gradually vary, hence, it is possible to change the flexural rigidity from the proximal side to the distal side. Accordingly, when the proximal tube 5 is applied to the ultrasound catheter 1 and the like, the high pushing or pressing-in property is exhibited by the proximal portion 52 having the high rigidity, the high tracking property along the lumen is exhibited while reducing a load to a living body by the soft distal portion 51, and thus, it is possible to improve the operability and it is also possible to prevent the bending without rapidly changing the rigidity of the sheath 2 along the axial direction. Particularly, since a force which tends to bend the sheath 2 by the guide wire 25 likely acts on the proximal side of the second guide wire lumen 26B, it is effective that the rigidity of the second guide wire lumen 26B on the proximal side is lowered along the inclination with a view of preventing the bending. Further, since the outer diameter, the inner diameter, and the thickness are all less in the distal portion 51 than the proximal portion 52, it is possible to set the physical properties (flexural rigidity and the like) by adjusting all of the outer diameter, the inner diameter, and the thickness, thereby amplifying the flexibility in the design.

Since the third outer diameter A13, the third inner diameter B13, and the third thickness D13 in the intermediate portion 53 gradually vary to be less from the proximal side toward the distal side, the flexural rigidity can gradually vary from the proximal side to the distal side in the intermediate portion 53 which varies in size, and thus, it is possible to further improve the operability and bending resistance thereof.

Also, since the proximal tube 5 is formed of the crystalline resin, it is possible to easily form a shape in which the outer diameter, the inner diameter, and the thickness are gradually decreased toward the distal side utilizing a shape changing of the crystalline resin by the annealing. In addition, utilizing the characteristics of the crystalline resin of which the rigidity varies due to crystallinity, it is possible to change the rigidity of the proximal tube 5 depending on a section.

That is, by lowering crystallinity of the distal portion 51 to be less than that of the proximal portion 52, it is possible to cause the distal portion 51 with the low crystallinity to have a soft structure likely deformed and cause the proximal portion 52 with the high crystallinity to have a structure unlikely deformed, and thus, it is possible to further improve the operability thereof.

The method of manufacturing the proximal tube 5 according to the exemplary embodiment includes a molding step of molding the intermediate body 9 with the crystalline resin in which the thickness D1 of the small diameter portion 91 is less than the thickness D2 of the large diameter portion 92, the outer diameter A1 of the small diameter portion 91 is equal to or less than the outer diameter A2 of the large diameter portion 92, and the thickness D3 of the inclined portion 93 between the small diameter portion 91 and the large diameter portion 92 gradually varies. Moreover, the exemplary manufacturing method as disclosed here includes an annealing step of forming the proximal tube 5 provided with the distal portion 51 which has the first outer diameter A11, the first inner diameter B11, and the first thickness D11; the proximal portion 52 which has the second outer diameter A12 greater than the first outer diameter A11, the second inner diameter B12 greater than the first inner diameter B11, and the second thickness D12 greater than the first thickness D11; and the intermediate portion 53 which is provided between the distal portion 51 and the proximal portion 52 and of which the outer diameter A13, the inner diameter B13, and the thickness D13 gradually vary, by annealing the intermediate body 9 to promote crystallization. Therefore, it is possible to easily manufacture the proximal tube 5 having the above-described shape by utilizing characteristics of the crystalline resin in which a diameter is likely reduced as a thickness of a section becomes thin when the annealing is performed, and by annealing the intermediate body 9 including the small diameter portion 91 having a thickness less than that of the large diameter portion 92.

Since the inner diameter of the intermediate body 9 is constant from the small diameter portion 91 to the large diameter portion 92, it is possible to easily form the intermediate body 9. Then, by simply performing the annealing of the intermediate body 9 of which the inner diameter is constant, and by utilizing the characteristics of the crystalline resin in which a diameter is likely reduced as a thickness of a section becomes thin when the annealing is performed as described above, it is possible to easily manufacture a member which differs in an outer diameter, an inner diameter, and a thickness depending on a section.

In the molding step, since the intermediate body 9 is molded by the extrusion molding, it is possible to easily manufacture the intermediate body 9 which is a tube with different diameters in which the outer diameter differs depending on a section.

In the annealing step, time for annealing the small diameter portion 91 is shorter than time for annealing the large diameter portion 92, and it is thus possible to enhance crystallinity of the proximal portion 52 to be greater than that of the distal portion 51 of the proximal tube 5 which is ultimately manufactured, and to enhance the flexural rigidity to be greater on the proximal side than on the distal side.

Note, however, that the disclosure here is not limited to the above-described exemplary embodiments, and it is possible to make various modifications. For example, in the above exemplary embodiments, although a case where the medical tube applied to a member configuring the ultrasound catheter as the proximal tube 5 is described, the disclosure herein can be applied to an optical probe (catheter) for a diagnostic apparatus utilizing light such as an optical coherence tomography diagnostic apparatus or an optical frequency domain imaging diagnostic apparatus, a balloon catheter, and the like. Moreover, the disclosure herein can be applied to all catheters as long as the catheter has a tubular body. In addition, in the exemplary embodiment, although crystallinity of the distal portion 51 is caused to be lower than crystallinity of the proximal portion 52, the disclosure here is not limited to such a configuration.

Figure 11:
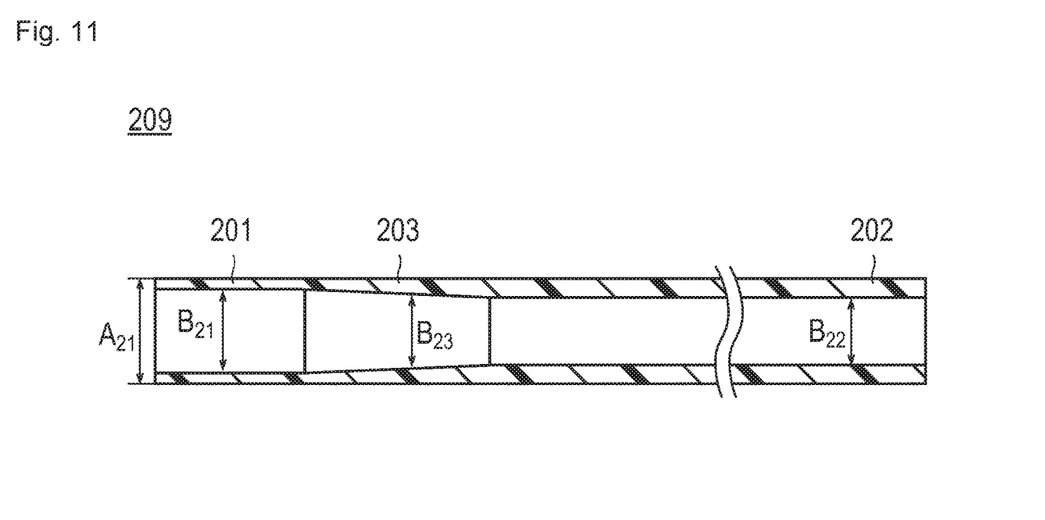
FIG. 11 is a cross-sectional view in the longitudinal direction illustrating an intermediate body which is a modification example.
Figure 12:
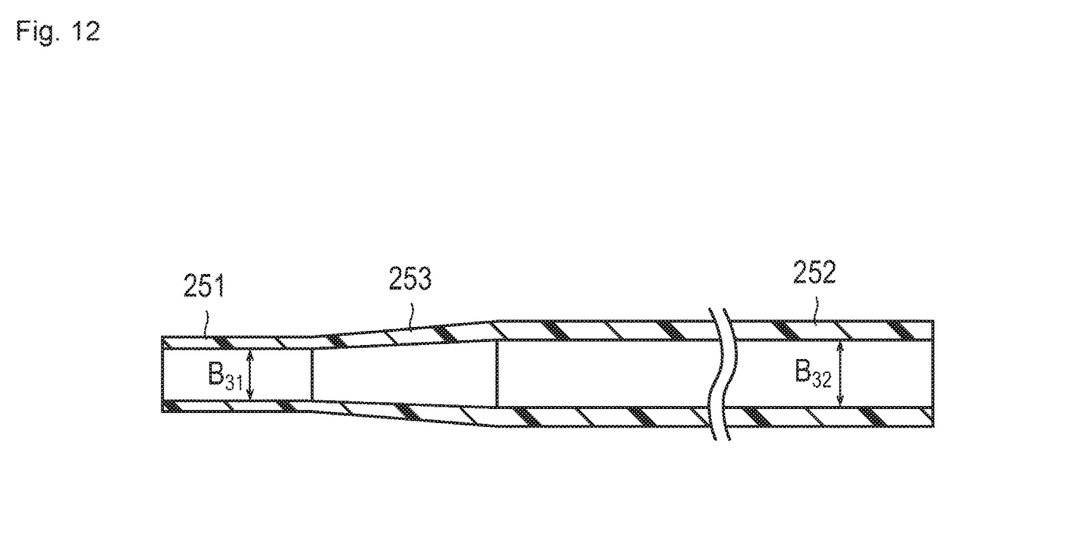
FIG. 12 is a cross-sectional view in the longitudinal direction illustrating a medical tube according to a further exemplary embodiment of the disclosure.

That is, as illustrated in FIG. 11, the annealing may be performed for an intermediate body 209 in which an inner diameter B21 of a first section 201 on one side is greater than an inner diameter B22 of a second section 202 on the other side, a third section 203 of which an inner diameter B23 gradually varies is provided between the first section 201 and the second section 202, and an outer shape A21 is constant from the first section 201 to third section 202. In this case as well, as illustrated in FIG. 12, the side of the first section which is thin in thickness is greatly reduced in diameter, and an inner diameter B31 of a distal portion 251 is contracted to be less than an inner diameter B32 of a proximal portion 252, and thus, it is possible to form a proximal tube of which an outer diameter, an inner diameter, and a thickness are decreased from a proximal side to a distal side. It is possible to easily mold such an intermediate body 209 employing the extrusion molding method, by sizing and regulating an outer peripheral surface of a molding object which is extruded from an extrusion port to maintain a constant outer diameter A21, and by changing a hauling speed of a hauler.

The method of molding an intermediate body is also not limited to the disclosed extrusion molding method, for example, and another method such as an injection molding method may be employed.

The detailed description above describes a medical tube, catheter and method of manufacturing the same disclosed by way of example. The disclosure is not limited, however, to the precise exemplary embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method of manufacturing a medical tube comprising:
molding a tubular intermediate body with a crystalline resin in which a thickness of a first section on one side is less than a thickness of a second section on the other side, an outer diameter of the first section is equal to or less than an outer diameter of the second section, and a third section is formed as gradually varying in thickness between the first section and the second section; and an annealing step of forming a distal portion which is provided on one end side and has a first outer diameter, a first inner diameter, and a first thickness, a proximal portion which is provided on the other end side and has a second outer diameter greater than the first outer diameter, a second inner diameter greater than the first inner diameter, and a second thickness greater than the first thickness, and an intermediate portion which is provided between the distal portion and the proximal portion and has an outer diameter, an inner diameter, and a thickness which gradually vary by annealing the intermediate body to promote crystallization.

2. The method of manufacturing a medical tube according to claim 1,
wherein an inner diameter of the intermediate body is constant from the first section to the second section.

3. The method of manufacturing a medical tube according to claim 1,
wherein the intermediate body is molded by extrusion molding in the molding step.

4. The method of manufacturing a medical tube according to claim 1,
wherein time for annealing the first section is shorter than time for annealing the second section in the annealing step.

5. The method of manufacturing a medical tube according to claim 1,
wherein said annealing step lowers crystallinity of the distal portion to be less than that of the proximal portion.

* * * * *